(12) United States Patent
Bornzin et al.

(10) Patent No.: US 8,706,224 B1
(45) Date of Patent: Apr. 22, 2014

(54) SYSTEMS AND METHODS FOR PAIRED/COUPLED PACING AND DYNAMIC OVERDRIVE/UNDERDRIVE PACING

(75) Inventors: Gene A. Bornzin, Simi Valley, CA (US); Joseph J. Florio, Bend, OR (US); Peter Boileau, Valencia, CA (US)

(73) Assignee: Pacesetter, In., Sylmar, CA (US)

( * ) Notice: Subject to any disclaimer, the term of this patent is extended or adjusted under 35 U.S.C. 154(b) by 843 days.

(21) Appl. No.: 11/929,719

(22) Filed: Oct. 30, 2007

(51) Int. Cl.
A61N 1/365 (2006.01)

(52) U.S. Cl.
USPC .............................. 607/25; 607/14

(58) Field of Classification Search
USPC ........................ 607/7, 9, 11, 14, 15
See application file for complete search history.

(56) References Cited

U.S. PATENT DOCUMENTS

| | | | |
|---|---|---|---|
| 3,857,399 A | 12/1974 | Zacouto | |
| 3,939,844 A | 2/1976 | Pequignot | |
| 4,674,508 A | 6/1987 | DeCote | |
| 5,213,098 A | 5/1993 | Bennett et al. | |
| 5,331,966 A * | 7/1994 | Bennett et al. | 600/508 |
| 5,480,413 A | 1/1996 | Greenhut et al. | |
| 5,643,327 A | 7/1997 | Dawson et al. | |
| 5,792,193 A | 8/1998 | Stoop | |
| 6,377,852 B1 | 4/2002 | Bornzin et al. | |
| 6,501,987 B1 | 12/2002 | Lovett et al. | |
| 6,606,517 B1 * | 8/2003 | Park et al. | 607/14 |
| 6,804,556 B1 * | 10/2004 | Florio et al. | 607/9 |
| 2002/0188328 A1 * | 12/2002 | Struble et al. | 607/9 |
| 2003/0004551 A1 * | 1/2003 | Chen et al. | 607/14 |
| 2003/0074029 A1 | 4/2003 | Deno et al. | |
| 2004/0049118 A1 | 3/2004 | Ideker et al. | |
| 2004/0049235 A1 | 3/2004 | Deno et al. | |
| 2006/0247700 A1 * | 11/2006 | Jackson | 607/9 |

FOREIGN PATENT DOCUMENTS

| | | |
|---|---|---|
| EP | 0550713 B1 | 10/1996 |
| WO | 9302745 A1 | 2/1993 |
| WO | 0158518 A2 | 8/2001 |
| WO | 0158518 A3 | 8/2001 |
| WO | 02053026 A2 | 7/2002 |
| WO | 02053026 A3 | 7/2002 |
| WO | 02053228 A1 | 7/2002 |
| WO | 03020364 A2 | 3/2003 |

OTHER PUBLICATIONS

Papageorgiou, Panos MD et al., "Coronary Sinus Pacing Prevents Induction of Atrial Fibrillation," Circulation. 1997;96:1893-1898.
Siddons, Harold and Sowton, Edgar, Cardiac Pacemakers. 1967:201-216.

* cited by examiner

*Primary Examiner* — Kennedy Schaetzle
*Assistant Examiner* — Erica Lee

(57) ABSTRACT

Techniques are described for use with an implantable cardiac stimulation device for performing paired/coupled pacing either alone or in conjunction with dynamic overdrive/underdrive pacing. In one technique, dynamic overdrive/underdrive pacing is delivered to the ventricles using paired pulses during an episode of atrial fibrillation. The use of paired pulses during dynamic ventricular overdrive/underdrive pacing helps lower and stabilize the ventricular rate to thereby reduce the risk of a ventricular arrhythmia. In another technique, the inter-pulse interval between paired pulses is optimized to lengthen the resulting refractory period to improve hemodynamics. Preferably, the optimized inter-pulse interval is used when applying dynamic ventricular overdrive/underdrive pacing with paired pulses so that the benefits of both techniques are obtained. The optimization technique is also applicable to setting the coupling interval for use with coupled pacing.

19 Claims, 9 Drawing Sheets

SYSTEMS AND METHODS FOR PAIRED/COUPLED PACING AND DYNAMIC OVERDRIVE/UNDERDRIVE PACING

FIELD OF THE INVENTION

The invention generally relates to implantable cardiac stimulation devices such as pacemakers and implantable cardioverter defibrillators (ICDs), and in particular, to techniques for pacing heart tissue using such devices.

BACKGROUND OF THE INVENTION

A pacemaker is an implantable medical device that recognizes various arrhythmias such as an abnormally slow heart rate (bradycardia) or an abnormally fast heart rate (tachycardia) and delivers electrical pacing pulses to the heart in an effort to remedy the arrhythmias. An ICD is an implantable device that additionally recognizes atrial fibrillation (AF) or ventricular fibrillation (VF) and delivers electrical shocks to terminate fibrillation. Pacemakers and ICDs detect arrhythmias by sensing internal electrical cardiac signals using leads implanted within the heart. The internal signals comprise an intracardiac electrogram (IEGM). Within the IEGM, the normal contraction of atrial heart muscle tissue appears as a P-wave whereas the normal contraction of ventricular muscle tissue appears as an R-wave (sometimes referred to as the "QRS complex"). More specifically, the P-wave corresponds to the electrical depolarization of atrial tissue and the R-wave corresponds to the depolarization of ventricular tissue. The subsequent electrical repolarization of the ventricular tissue appears within the IEGM as a T-wave. Strictly speaking, P-waves, R-waves and T-waves are features of a surface electrocardiogram (EKG or ECG). For convenience, the terms P-wave, R-wave and T-wave are also used herein to refer to the corresponding internal signal component.

AF is a type of atrial tachycardia wherein the atria of the heart beat chaotically. During an episode of AF, patients often feel heart palpitations, fainting, dizziness, weakness, shortness of breath and angina pectoris (chest pain caused by a reduced blood supply to the heart muscle). Though not life threatening, AF can be quite unpleasant for the patient and so it is desirable to prevent AF from occurring. Moreover, the irregular beating of the atria during AF interferes with the proper hemodynamic function of the heart by preventing the ventricles from filling properly. As a result, optimal ventricular pressure is not achieved during each heartbeat and overall cardiac performance is degraded, i.e. the ventricles do not efficiently pump blood into the circulatory system. The ventricular rate may become somewhat erratic as well, due to conduction from the atria to the ventricles, possibly triggering a ventricular tachyarrhythmia. Furthermore, during AF, blood tends to pool in the heart chambers, increasing the risk of a blood clot forming inside the heart. Once formed, a blood clot can travel from the heart into the bloodstream and through the body, potentially becoming lodged in an artery, possibly causing a pulmonary embolism or stroke. Hence, steps are preferably taken to prevent the occurrence AF and, should an episode of AF nevertheless occur, it is deemed advisable, at least conventionally, to terminate the episode as soon as possible.

One technique for attempting to prevent AF from occurring is "overdrive pacing" wherein an implantable cardiac stimulation device, such as a pacemaker or ICD, applies electrical pacing pulses to the atria at a rate somewhat faster than the intrinsic atrial rate of the patient. It is believed that overdrive pacing is effective for at least some patients for preventing AF for the following reasons. A normal, healthy heart beats only in response to electrical pulses generated from a portion of the heart referred to as the sinus node. The sinus node pulses are conducted to the various atria and ventricles of the heart via certain, normal conduction pathways. In some patients, however, portions of the atria also generate electrical pulses referred to as "ectopic" pulses. Each pulse, whether a sinus node pulse or an ectopic pulse, has a refractory period subsequent thereto, during which time heart tissue is not responsive to any electrical pulses. A combination of sinus pulses and ectopic pulses can result in a dispersion of the refractory periods within the atria which, in turn, can trigger AF. By overdrive pacing the atria at a uniform rate, the likelihood of the occurrence of ectopic pulses is reduced and the refractory periods within the heart tissue are rendered uniform and periodic. Thus, the dispersion of refractory periods is reduced and the risk of AF is thereby also reduced. With overdrive pacing in the atria, it is desirable to achieve a high percentage of overdrive paced beats so as to reduce the likelihood of ectopic beats.

A particularly effective overdrive pacing technique for the atria, referred to herein as dynamic atrial overdrive (DAO) pacing, is described in U.S. Pat. No. 6,519,493 to Florio et al., entitled "Methods and Apparatus for Overdrive Pacing Heart Tissue Using an Implantable Cardiac Stimulation Device", which is incorporated by reference herein. With DAO, the overdrive pacing rate is controlled to remain generally uniform and, in the absence of a tachycardia, is adjusted upwardly or downwardly only occasionally in response to breakthrough sinus beats. The aggressiveness of overdrive pacing may be modulated by adjusting the overdrive pacing rate and related control parameters. See: U.S. Pat. Nos. 6,968, 232 and 7,006,868, both of Florio et al., entitled "Method And Apparatus For Using A Rest Mode Indicator To Automatically Adjust Control Parameters Of An Implantable Cardiac Stimulation Device", and both filed Mar. 6, 2002; U.S. patent application Ser. No. 10/043,781, also of Florio et al., entitled "Method And Apparatus For Dynamically Adjusting A Non-Linear Overdrive Pacing Response Function", filed Jan. 9, 2002; and U.S. Pat. No. 6,904,317, of Falkenberg et al., entitled "Method And Apparatus For Dynamically Adjusting Overdrive Pacing Parameters", filed Jan. 9, 2002. Capture of overdrive pulses may be verified as set forth in U.S. Pat. No. 7,062,327, of Bradley et al., entitled "Method And Apparatus For Providing Atrial AutoCapture In A Dynamic Atrial Overdrive Pacing System For Use In An Implantable Cardiac Stimulation Device", filed May 2, 2002.

Thus, atrial overdrive pacing, particularly DAO, provides a useful technique for helping to prevent the onset of AF. Should an episode of AF nevertheless occur, cardioversion is typically employed to terminate the episode, i.e. strong electrical shocks are delivered to the atria in an attempt to revert the atria from fibrillation to a normal sinus rhythm. Typically, each cardioversion shock delivers about two joules of energy to the atria. Cardioversion techniques are described in U.S. Pat. No. 6,445,949 to Kroll, entitled "Implantable Cardioversion Device with a Self-Adjusting Threshold for Therapy Selection".

Although cardioversion is generally effective in terminating AF, in many cases fibrillation soon resumes, requiring another round of shocks. Repeated shocks are quite painful to the patient and can deplete battery resources of the implanted device. One reason cardioversion shocks are painful is that the patient is typically conscious and alert at the time the shock is administered. This is in contrast with stronger defibrillation shocks provided for terminating ventricular fibrillation (VF), which are typically not administered until the patient has lost consciousness. Because AF is not usually immediately life threatening, painful shocks for its treatment may be perceived by patients as worse than the disease itself and therefore not tolerated. Indeed, anxiety arising in a patient from the fear of receiving multiple, painful cardioversion shocks may be sufficient to raise the heart rate sufficiently to trigger such shocks.

As some patients have hundreds of AF episodes annually, it is desirable to provide techniques for pacing the heart during AF in such a way that the adverse effects of AF are mitigated without requiring delivery of cardioversion shocks. In particular, it is desirable to pace the heart during AF so as to improve hemodynamic performance to thereby reduce adverse symptoms suffered by the patient and reduce the risk of blood clots. It is to these ends that aspects of the invention are generally directed.

One technique that has been proposed for treating AF without cardioversion is to apply overdrive pacing to the ventricles during an episode of AF. That is, atrial overdrive pacing is applied in an attempt to prevent an episode of AF from occurring, but should one nevertheless occur, atrial overdrive pacing is deactivated and ventricular overdrive pacing is instead performed. Unlike atrial overdrive pacing, where it is generally desirable to achieve a high percentage of overdrive paced beats, ventricular overdrive pacing is preferably performed to achieve rate smoothing, i.e. to reduce or eliminate any significant changes in ventricular rate occurring over short periods of time. One advantage of stabilizing the ventricular rate during AF is that it reduces the likelihood of a more serious ventricular tachyarrhythmia be reducing conduction from the atria to the ventricles. A particularly effective technique for performing ventricular overdrive pacing for the purposes of rate smoothing is "dynamic ventricular overdrive" (DVO), which is described in U.S. patent application Ser. No. 10/456,060, to Park et al., entitled "System And Method For Dynamic Ventricular Overdrive Pacing", filed Jun. 6, 2003, and which is incorporated by reference herein. Note that, with DVO, the ventricular overdrive rate need not be faster than the intrinsic ventricular rate, i.e. "overdrive" pacing in the ventricles can be used to actually reduce the ventricular rate (i.e. to "underdrive" the ventricles). For generality herein, the term "dynamic overdrive/underdrive pacing" is used to refer to a pacing procedure wherein pacing is delivered at a rate selected to permit detection of at least some intrinsic pulses and wherein the rate is automatically and selectively controlled in response to the detected intrinsic pulses to achieve desired overdrive and/or underdrive pacing. (Note that, underdrive pacing is sometimes more narrowly defined as "a method for terminating certain tachycardias by means of slow asynchronous pacing at a rate that is not an even fraction of the tachycardia rate". This narrow definition is not used herein. Rather, underdrive pacing is broadly defined herein as pacing the heart (or selected chambers thereof) so as to achieve a rate generally lower than the intrinsic rate that would otherwise be exhibited.)

Although the use of dynamic ventricular overdrive/underdrive pacing, particularly the techniques set forth in the aforementioned application to Park et al., has been found to be effective for mitigating some of the problems caused by AF, considerable room for improve remains. In particular, although the rate smoothing achieved by dynamic ventricular overdrive/underdrive pacing may be effective in stabilizing the ventricular rate so as to reduce the risk of a ventricular tachyarrhythmia, smoothing of the ventricular rate does not necessarily serve to achieve optimal ventricular hemodynamic performance during each individual heart beat. Hence, overall cardiac performance can still be significantly degraded during AF. Moreover, blood can still pool in the ventricles, causing risk of blood clots.

Accordingly, it would be desirable to provide improved techniques for pacing the ventricles—particularly for use during AF—that serve to improve the pumping effectiveness of the ventricles during each individual heart beat so as to improve overall hemodynamic performance. It is to this end that aspects of the invention are particularly directed.

SUMMARY OF THE INVENTION

In accordance with a first exemplary embodiment, an improvement is provided for use within an implantable cardiac stimulation device capable of performing overdrive pacing. The improvement generally comprises delivering dynamic overdrive/underdrive pacing using paired pacing pulses. Paired pacing is a pacing technique whereby a secondary pacing pulse is delivered shortly following a primary pacing pulse—typically about 300 milliseconds (ms) later. The primary pulse triggers both an electrical depolarization of myocardial tissue and a corresponding mechanical contraction. The secondary pulse, if properly timed, has the effect of electrically depolarizing the myocardial tissue without causing a second mechanical myocardial contraction. In other words, both the primary and secondary pulses trigger separate electrical evoked responses, but only the primary pulse causes an actual mechanical contraction of a portion of the heart. This phenomenon is known as pulseless electrical activity (PEA.) Paired pacing, among other advantages, can prolong the refractory period associated with myocardial depolarization so as to permit pacing the heart at a rate slower than the intrinsic rate by delaying spontaneous depolarizations. Such prolongation of refractory periods can also affect calcium release so as to improve myocardial contractility.

By delivering dynamic overdrive/underdrive pacing using paired pacing pulses, the benefits of both pacing techniques can be advantageously combined. For example, if dynamic ventricular overdrive/underdrive pacing is provided for ventricular rate smoothing during an episode of AF, the extension of ventricular refractory periods achieved with paired pacing in the ventricles can reduce conduction from the atria to the ventricles to thereby improve ventricular tachyarrhythmia suppression and can also achieve lower, smoother ventricular rates so as to reduce palpitations felt by the patient. If DAO pacing is provided so as to prevent atrial ectopic beats for AF suppression purposes, the extension of refractory periods achieved with paired pacing in the atria can further reduce the likelihood of atrial ectopic beats, thus permitting more effective AF suppression to be achieved at a lower atrial overdrive rate.

In accordance with a second exemplary embodiment, an improvement is provided for use within an implantable cardiac stimulation device capable of performing paired pacing. The improvement comprises the delivery of paired pacing with an interval set sufficient to ensure that an evoked response associated with a secondary pulse is wider than an evoked response associated with a primary pulse of the pair of pulses. By timing the secondary pulse in such a manner, improved hemodynamic performance can be achieved, e.g. improved left ventricular (LV) pressure can be achieved and an improved change in pressure with time (dP/dt) can also be achieved. The improved inter-pulse interval is advantageously applied during the delivery of dynamic ventricular overdrive/underdrive pacing during AF so as to improve the hemodynamic performance of the ventricles during each ventricular beat, but is not limited for use with overdrive/underdrive pacing. Indeed, the improved inter-pulse interval may be advantageously employed whenever paired pacing is appropriate, in either the ventricles or the atria.

The second embodiment is also applicable to coupled pacing. With coupled pacing, a "secondary" pulse is delivered subsequent to an intrinsic depolarization, rather than subsequent to a primary pacing pulse. As with paired pacing, coupled pacing can prolong the refractory period and cause a slowing of heart rate by increasing the interval between spontaneous depolarizations. When applied to coupled pacing, the improvement of the invention comprises the delivery of coupled pacing with an interval set sufficient to ensure that an evoked response associated with a coupled pulse is wider than the preceding intrinsic depolarization. By timing the coupled pulse in such a manner, improved hemodynamic performance can also be achieved. The improved coupling interval is advantageously employed whenever coupled pacing is otherwise appropriate. (Note that, unlike paired pacing, coupled pacing is not preferably performed in conjunction with dynamic overdrive/underdrive pacing since coupled pacing relies on intrinsic depolarizations, which are to be avoided during dynamic overdrive/underdrive pacing.)

Other aspects, features, and advantages of the invention will be apparent from the detailed description that follows in the combination with the attached drawings. Method, system and apparatus embodiments of the invention are also provided.

BRIEF DESCRIPTION OF THE DRAWINGS

The above and further features, advantages and benefits of the invention will be apparent upon consideration of the present description taken in conjunction with the accompanying drawings, in which.

DESCRIPTION OF THE PREFERRED EMBODIMENTS

The following description includes the best mode presently contemplated for practicing the invention. This description is not to be taken in a limiting sense but is made merely for the purpose of describing the general principles of the invention. The scope of the invention should be ascertained with reference to the issued claims. In the descriptions that follow, like numerals or reference designators will be used to refer to like parts or elements throughout.

Figure 1:
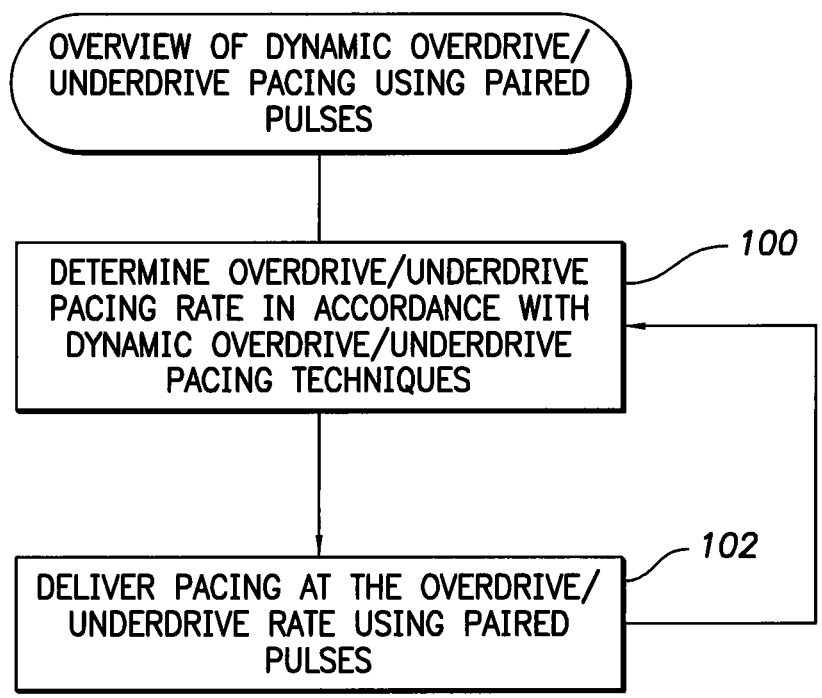
FIG. 1 is a flow diagram providing an overview of a technique for performing paired pacing in conjunction with dynamic overdrive/underdrive pacing.
Figure 2:
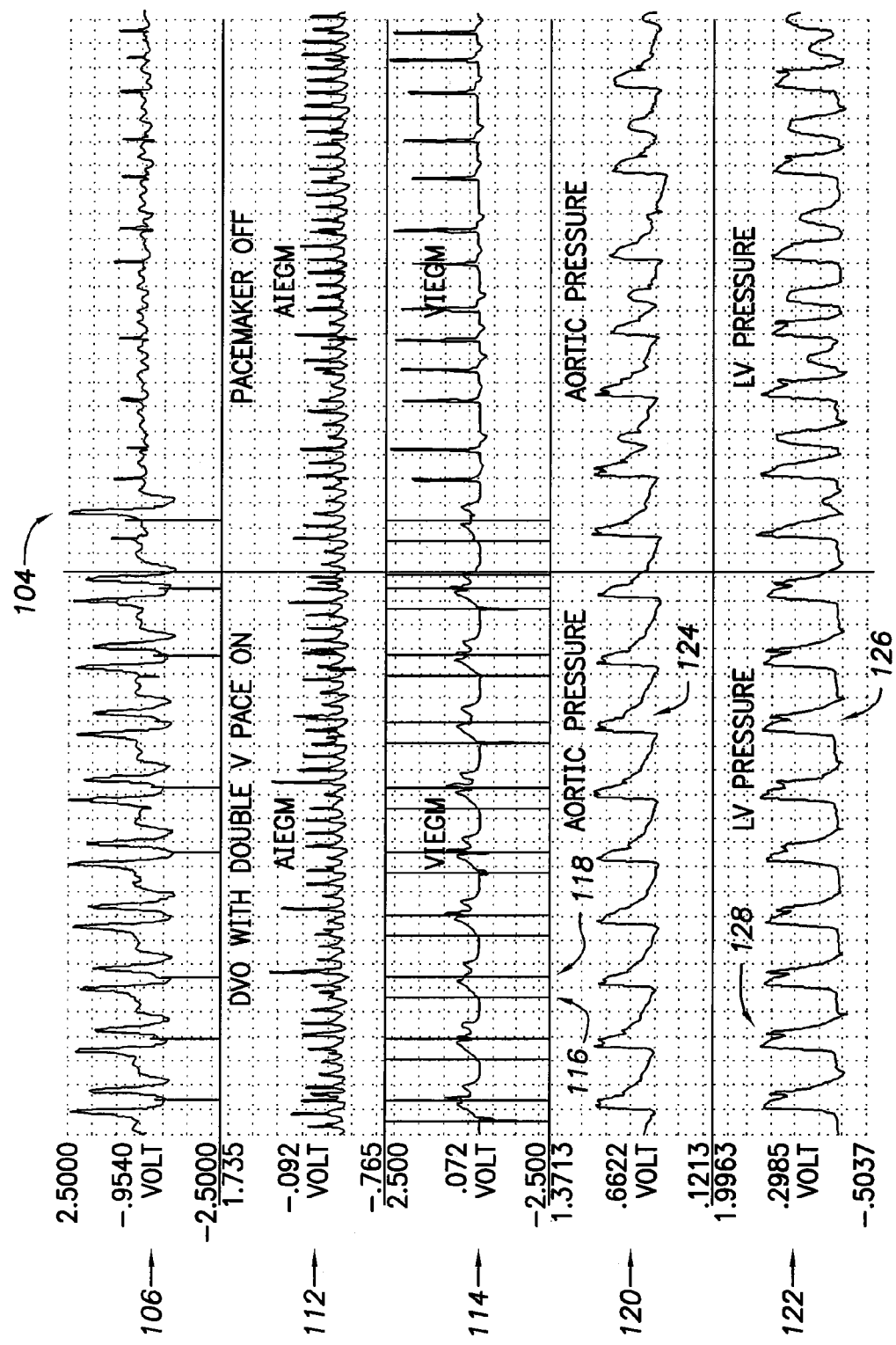
FIG. 2 is a diagram of exemplary traces of EKG, atrial IEGM, ventricular IEGM, aortic pressure and LV pressure, particularly illustrating the use of dynamic ventricular overdrive/underdrive pacing during an episode of AF, in accordance with the general techniques of FIG. 1.

Briefly, techniques for performing paired pacing in conjunction with dynamic overdrive/underdrive pacing are discussed with respect to FIGS. 1-2. Techniques for performing paired/coupled pacing with optimal inter-pulse intervals are discussed with respect to FIGS. 3-6. Exemplary techniques for performing paired pacing in conjunction with dynamic ventricular overdrive/underdrive pacing during AF while also using optimal inter-pulse intervals are discussed with respect to FIG. 7. An overview of an exemplary implantable cardiac stimulation device, equipped to implement one or more of the techniques of FIGS. 1-7, is then summarized with reference to FIGS. 8-9.

Overview of Paired Pacing During Dynamic Overdrive/Underdrive Pacing

FIG. 1 broadly summarizes techniques for performing paired pacing during dynamic overdrive/underdrive pacing. At step 100, an implantable cardiac stimulation device (e.g. pacemaker or ICD) determines an overdrive/underdrive pacing rate in accordance with dynamic overdrive/underdrive pacing procedures or techniques. At step 102, the device delivers paired pacing pulses to the heart of the patient at the overdrive/underdrive pacing rate, i.e. the device delivers both a primary and a secondary pulse in circumstance wherein only a single pulse would be delivered in accordance with non-paired dynamic overdrive/underdrive techniques. The overdrive/underdrive rate is used to specify the timing intervals between consecutive primary pulses. The inter-pulse intervals between the primary and secondary pulse of each pair of pulses may be set in accordance with otherwise conventional paired pacing techniques. Preferably, however, the interval is set in accordance with the improved techniques discussed below with reference to FIGS. 3-6. In any case, once a pair of pulses is delivered, step 102 is again performed to adjust the overdrive/underdrive rate, if needed, before another pair of pulses is delivered. Steps 100-102 are repeated in this manner until the device deactivates dynamic overdrive/underdrive pacing w/paired pulses and instead performs pacing in accordance with some other pacing mode. Conditions for activating and deactivating dynamic overdrive/underdrive pacing w/paired pulses are discussed in more detail below with reference to FIG. 7. Preferably, dynamic overdrive pacing is delivered only up to some predetermined maximum rate. Likewise, dynamic underdrive pacing is delivered only down to some predetermined minimum rate.

As noted, paired pacing is a pacing technique whereby a secondary pacing pulse is delivered shortly following a primary pacing pulse. The primary pulse triggers both an electrical depolarization of myocardial tissue and a corresponding mechanical contraction. The secondary pulse, if properly timed, electrically depolarizes the myocardial tissue but does not cause a second mechanical myocardial contraction. Paired pacing, among other advantages, can prolong the refractory period associated with myocardial depolarization so as to permit pacing the heart at a rate slower than the intrinsic rate by delaying spontaneous depolarizations. Note that, with paired pacing, the paired pulses are typically both delivered using the same electrode within the same chamber of the heart, e.g. both are delivered via a right ventricular (RV) tip electrode. This is in contrast with cardiac resynchronization techniques (CRT) wherein a pair of pulses is delivered using different leads in different chambers of the heart. (Typically, with CRT, a pair of pulses is delivered separately in the left and right ventricles. The inter-pulse delay between the RV pulse and the LV pulse is set to ensure that both pulses achieve both an electrical depolarization and a corresponding mechanical depolarization. With paired pacing, as noted, the timing between the pulses is preferably set so that the second pulse of the pair triggers an electrical depolarization but does not trigger a mechanical contraction.)

In one example, the paired pacing with dynamic overdrive/underdrive pacing of FIG. 1 is applied to the atria for AF suppression purposes, i.e. to prevent the onset of AF. In another example, it is instead applied to the ventricles during AF to stabilize the ventricles to reduce the risk of ventricular tachyarrhythmias and to reduce heart palpitations. If intended for use in the atria, DAO techniques described in the above-referenced patent to Florio et al. (U.S. Pat. No. 6,519,493) are preferably employed in determining the atrial overdrive rate. If intended for use in the ventricles, techniques described in the above-referenced patent application to Park et al. (U.S. patent application Ser. No. 10/456,060) are instead preferably employed to determine the ventricle overdrive rate. These techniques are preferred, in part, because they allow for a determination of the overdrive/underdrive rate based only on the presence or absence of intrinsic "breakthrough" beats and do not necessarily require a determination of the underlying intrinsic rate. No significant modification is required in the manner by which these techniques operate to determine the overdrive/underdrive rate to accommodate paired pulses. However, other techniques for determining atrial or ventricular overdrive/underdrive rates, including techniques that require determining the underlying intrinsic rate, may alternatively be employed at step 100. Such techniques may need to be modified to account for the longer refractory periods caused by the use of paired pacing pulses. In some cases, the overdrive/underdrive rate for use with paired pulses may need to be specifically set to a lower rate than the overdrive/underdrive rate for use with single pulses to account for the longer refractory periods caused by paired pacing.

By employing dynamic overdrive/underdrive pacing in conjunction with paired pacing, the benefits of both are combined and enhanced. Briefly, with DAO, an increase in the atrial dynamic overdrive pacing rate is performed only in response to detection of at least two intrinsic atrial beats within a predetermined search period. In one specific technique, an increase in the atrial pacing rate occurs only if two intrinsic P-waves (also called breakthrough beats) are detected within X cardiac cycles of one another. In another specific technique, the overdrive rate is increased only if at least two P-waves (or breakthrough beats) are detected within a block of N consecutive cardiac cycles. The increase is by an amount Y. With both techniques, the overdrive rate is automatically decreased by an amount W if no increase has occurred in the last Z cardiac cycles. X, Y, Z, N and W are all programmable values. X is typically in the range of 8 to 40 cardiac cycles. Y, the rate increase, is typically in the range of 5-25 pulses per minute (ppm). Z, the dwell time before the rate is decreased, is typically in the range of 8 to 40 cardiac cycles. W, the rate decrease, is typically in the range of 1-5 ppm/cardiac cycle. Similar rate adjustment techniques are employed in dynamic ventricular overdrive/underdrive pacing.

As noted, paired pacing serves to increase the duration of the refractory periods. Hence, when paired pacing is performed in conjunction with dynamic overdrive/underdrive pacing, the increase in the duration of the refractory periods serves to reduce the occurrence of breakthrough beats. Since overdrive rates are adjusted upwardly in accordance with dynamic overdrive/underdrive only in response to intrinsic breakthrough beats, the increase in the duration of the refractory periods caused by paired pacing yields a generally lower and more stable overdrive rate. This difference arises automatically as a result of the operation of the dynamic overdrive/underdrive pacing rate adjustment algorithm in response to fewer breakthrough beats. A lower and smoother rate may also be achieved with paired pacing when using other overdrive/underdrive rate determination techniques, depending upon the particular technique.

Hence, the use of paired pacing along with dynamic overdrive/underdrive pacing can achieve a generally lower and more stable rate. For DAO, this may aid in the suppression of AF by reducing the number of ectopic atrial beats. For dynamic ventricular overdrive/underdrive pacing, this may aid in the suppression of ventricular tachyarrhythmias by reducing the number of ventricular beats triggered by conduction from the atria to the ventricles during AF. For both, the generally lower and smoother rates serve to reduce perceptible heart palpitations, reduce power consumption (due to lower pacing rate), and improve hemodynamic performance of the heart.

An example of the use of dynamic overdrive/underdrive pacing with paired pacing pulses is shown in FIG. 2, for a specific case wherein dynamic ventricular overdrive/underdrive pacing was performed during an episode of AF. A series of traces derived from a test subject via an implanted device and a surface EKG device are shown. Initially, the implanted pacemaker delivers paired pacing pulses in the ventricles at a rate specified by otherwise routine dynamic ventricular overdrive/underdrive pacing. At time 104, dynamic ventricular overdrive/underdrive pacing is deactivated. Thereafter, the ventricles beat in accordance with intrinsic QRS complexes. Note that no pacing is applied directly to the atria at any time during the traces. AF continues throughout the entire period of time.

Now considering the traces in greater detail, trace 106 illustrates the surface EKG obtained during the episode of AF. Electrical complexes appearing within the EKG are much larger while dynamic ventricular overdrive/underdrive pacing is performed than after it is deactivated simply because of the presence of the ventricular pacing pulses themselves. A second trace 112 illustrates the atrial IEGM signal (sensed internally); whereas a third trace 114 illustrates the ventricular IEGM signal (also sensed internally). The atrial rate appearing within the atrial IEGM is fast and chaotic due to AF. The ventricular IEGM illustrates pairs of pacing pulses (116 and 118, for example), which are spaced slightly apart. The paired ventricular pacing pulses were delivered to the right ventricle at a rate specified by dynamic ventricular overdrive/underdrive pacing techniques. Note that the overdrive/underdrive rate for the ventricular pulses specifies the interval from a first pulse of one pair to the first pulse of the next pair—not the interval between the first and second pulse of a given pair, which is referred to herein as the inter-pulse interval. Note also that the ventricular pacing rate is slower than the concurrent atrial rate, which is subject to fibrillation. Aortic pressure is illustrated by trace 120 and LV pressure is illustrated by trace 122.

As can be seen, during the initial period of time when paired pacing is performed in conjunction with dynamic ventricular overdrive/underdrive pacing, a strong peak in aortic pressure, 124, is associated with each pair of ventricular pacing pulses. Likewise, a strong peak in left ventricular pressure, 126, is associated with each pair of ventricular pacing pulses. In other words, the ventricles are beating fairly effectively despite AF. However, once dynamic ventricular overdrive/underdrive pacing is deactivated, at time 104, both the aortic pressure profile and the left ventricular pressure profile are degraded, indicating less effective ventricular action. More specifically, some ventricular contractions achieve relatively high LV pressure; whereas others achieve much lower LV pressure. As a result, peak aortic pressure is generally reduced. Compare, for example, the aortic pressure profile before time 104 as opposed to after time 104.

The erratic LV pressure profile occurring after time 104 is due to erratic ventricular mechanical contractions trigged by unevenly-spaced ventricular depolarizations. The erratic ventricular depolarizations are shown most clearly in the ventricle IEGM. They are erratic both in terms of spacing and magnitude. The ventricular depolarizations are erratic due to conduction of fibrillatory P-waves from the atria to the ventricles. In this regard, the ventricles are refractory for a short period of time following each ventricular depolarization, during which the ventricles will not contract in response to electrical stimulation. Some of the P-waves reach the ventricles while the ventricles are still refractory and have no effect. Others reach the ventricles while the ventricles are non-refractory and hence trigger at least a partial mechanical contraction. Since the timing and magnitude of the P-waves are erratic due to AF, the timing and magnitude of the ventricular depolarizations they trigger are also somewhat erratic. Erratic beating of the ventricles undermines the hemodynamic performance of the ventricles and so both LV pressure and aortic pressure is degraded.

In contrast, during the initial period of time while dynamic ventricular overdrive/underdrive pacing with paired pacing is performed, the extension of ventricular refractory periods achieved by virtue of paired pacing helps prevent P-waves from the atria from triggering ventricular depolarizations, i.e. the ventricles are more likely to be refractory when P-waves are conducted to the ventricles and so those P-waves have no effect. Hence, the ventricles can beat at a fairly constant rate specified by the overdrive rate, improving the hemodynamics of each ventricular contraction, thus improving both LV pressure and aortic pressure.

Thus, the traces of FIG. 2 illustrate that improved LV pressure and aortic pressure can be obtained during AF by employing paired pacing pulses along with dynamic ventricular overdrive/underdrive pacing. Although the traces of FIG. 2 are merely exemplary and have been derived from a subject under test conditions, it is believed that similar improvements in LV pressure and aortic pressure can also be obtained within typical patients subject to actual episodes of AF.

Finally, with respect to FIG. 2, note that most of the LV pressure peaks prior time 104 exhibit a slight notch, such as notch 128. The notch is due to slightly uneven contraction of the ventricles resulting from a non-optimal inter-pulse delay. Techniques for optimizing the inter-pulse interval for use with paired pacing (or coupled pacing) will now be described.

Overview of Paired/Coupled Pacing with Optimal Inter-Pulse Intervals

Figure 3:
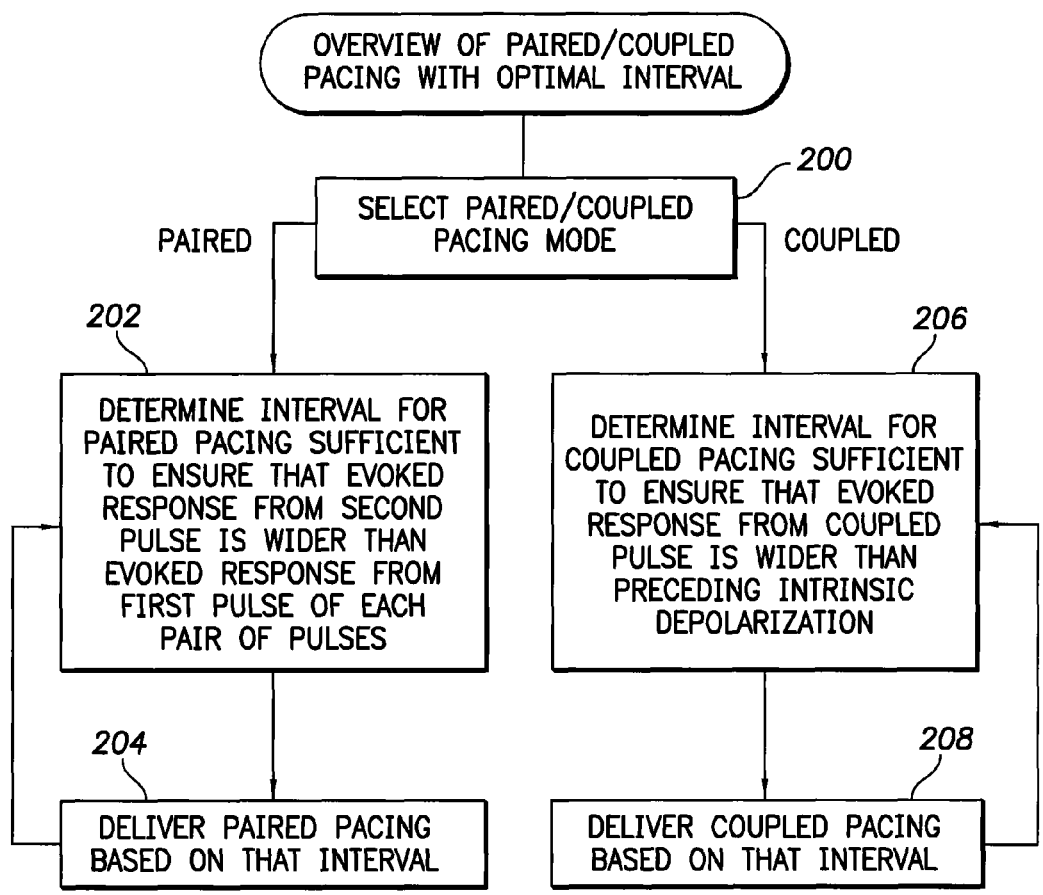
FIG. 3 is a flow diagram providing an overview of a technique for performing paired/coupled pacing with an optimal inter-pulse interval.

Turning now to FIG. 3, techniques for optimizing inter-pulse delay for use with paired pacing or coupled pacing will be described. These techniques need not be used only during dynamic overdrive/underdrive pacing but may be advantageously exploited wherever paired pacing or coupled pacing is otherwise appropriate. Beginning at step 200, the implanted device selects either paired pacing or coupled pacing in accordance with the needs of the patient and the programming of the device. If paired pacing is selected then, beginning at step 202, the device first determines the inter-pulse interval for paired pacing sufficient to ensure that an evoked response from a second pulse of the pair of pulses is wider than the evoked response from the first pulse of the pair of pulses. It is believed that this inter-pulse interval is optimal because is provides the longest refractory period, which is beneficial for many applications, such as with dynamic overdrive/underdrive pacing. Any suitable measure of the width of the evoked response may be used, such as the duration during which the absolute magnitude of the evoked response exceeds some predetermined voltage. In one specific technique, a paced depolarization integral (PDI) is employed to help quantify the width of each evoked response. PDI is discussed in U.S. Pat. No. 5,643,327 to Dawson, et al., which is incorporated herein by reference.

The determination of step 202 may be made, for particular patient, by adjusting the inter-pulse interval through a range of values while measuring and comparing the width of the associated evoked responses. The value of the inter-pulse interval that provides the longest width for the evoked response of the second pulse relative to the evoked response of the first pulse is then stored in the implantable device for subsequent use during paired pacing. The optimal interval may depend upon the pacing rate. Hence, the optimization procedure may be repeated for different pacing rates with different optimal values determined and stored for use with different ranges of pacing rates. Alternatively, a single value may be determined for use at a base pacing rate, and then adjusted by the implanted device based upon the amount by which the current pacing rate exceeds the base rate. Routine experimentation may be performed to determine an appropriate adjustment factor. Depending upon the particular implementation, optimal inter-pulse interval values may be determined during an initial programming session between physician and patient or, if the device is so equipped, the device itself may periodically perform an optimization procedure to update the optimal interval values within the patient so as to automatically compensate for any physiological or anatomical changes within the patient, such as changes resulting from progression of heart disease. Alternatively, the interval between first and second pulses can be set to the shortest duration that ensures that the second pulse does not trigger a mechanical contraction of a chamber of the heart to which it is applied. Then, at step 204, the device begins delivering paired pacing pulses using the interval determined at step 202. Paired pacing may be performed in accordance with otherwise conventional paired pacing techniques or in conjunction with dynamic overdrive/underdrive pacing, as has already been discussed.

Alternatively, if coupled pacing is to be performed then, beginning at step 206, the device determines the interval for coupled pacing sufficient to ensure that the evoked response from the coupled pulse is wider than the intrinsic depolarization. It is believed that this coupling interval is optimal because is provides the longest combined refractory period, which is beneficial for many applications. Again, any appropriate technique may be employed for quantify the width of the intrinsic depolarization. The determination of the optimal coupling interval may be made, for a particular patient, by adjusting the coupling interval through a range of values while measuring the width of both the intrinsic depolarization and the evoked response of the coupled pulse. This interval is adjusted until the evoked response from the coupled pulse is found to be wider than the intrinsic depolarization to which it is coupled. The value of the inter-pulse interval that provides the longest width for the evoked response of the coupled pulse relative to the width of the intrinsic depolarization is the optimal interval and is stored in the implantable device for subsequent use during coupled pacing.

Similar to paired pacing, the optimal interval associated with coupled pacing may depend upon the intrinsic rate, with higher intrinsic rates typically necessitating a shorter coupling interval. Hence, the coupling interval optimization procedure may be repeated for different intrinsic rates with different optimal values determined and stored for use with different ranges of intrinsic rates. Alternatively, a single value may be determined for use at a rest pacing rate, and then adjusted by the implanted device based upon the amount by which the current intrinsic rate exceeds the rest rate. Routine experimentation may be performed to determine an appropriate adjustment factor. In addition, as with paired pacing, depending upon the particular implementation, optimal coupling interval values may be determined during an initial programming session or, if the device is so equipped, the device itself may periodically perform an optimization procedure to update the optimal coupling values within the patient. In any case, beginning at step 208, the device then begins delivering coupled pacing using the interval determined at step 206.

Thus, FIG. 3 summarizes an optimization technique for determining an optimal or preferred inter-pulse delay for paired pacing or an optimal or preferred coupling interval for coupled pacing. The optimal intervals may generally be used whenever paired or coupled pacing would otherwise be deemed appropriate, subject to physician approval. In this regard, many uses for paired/coupled pacing techniques have been proposed. Siddons and Sowton (*Cardiac Pacemakers.* 1967:201-216) have proposed that paired/coupled pacing may be used to provide continuous extra-systolic augmentation and indeed cardiac performance has been found to be enhanced by this therapy. The objective is to treat heart failure and to enhance cardiac performance in congestive heart failure (CHF). It proved to be effective in these patients but there was great concern that an extra-stimulus provided in the ventricles of patients would create excessive arrhythmic risk, particularly fibrillation. Such patients are already susceptible to arrhythmias and may be put at an even greater risk by stimulating near the vulnerable period. The extension of refractory periods provided when using the optimal inter-pulse interval of the invention may be beneficial in reducing the risk of such arrhythmias. Coupled pacing has also been used for treatment of ventricular and atrial tachyarrhythmias in which a stimulus is coupled to a spontaneous depolarization and set to a fraction of the spontaneous cardiac interval as taught by Zacouto (U.S. Pat. No. 3,857,399) and Pequignot (U.S. Pat. No. 3,939,844). This effectively slows the heart during an arrhythmia.

Paired pacing has been proposed in the atrium to augment ventricular contraction but was not found to be as effective as paired ventricular stimulation. Bornzin et al. (U.S. Pat. No. 6,377,852) has proposed that paired stimulation of the atrium may be used to increase the atrial refractory period and prevent premature atrial contractions (PACs) from the left atrium (LA) from triggering reentrant atrial arrhythmias. This technique may be especially effective during LA pacing since it has been shown that inducing atrial arrhythmias from the right atrium is very difficult. Papageorgiu showed that pacing from distal coronary sinus (CS) caused low atrial depolarization rendering it refractory to premature stimuli delivered from HRA and precluded induction of atrial fibrillation. (Papageorgiu et al., "Coronary sinus pacing prevents induction of atrial fibrillation," CIRC, 1997; 96:1893-1989.) Bornzin has also suggested that paired pacing in the atrium may be used to slow the overall rate to allow more time for filling the ventricle, which may be useful in enhancing stroke volume in patients with diastolic dysfunction.

The following patents and patent applications also discuss paired pacing and related techniques: U.S. Pat. No. 4,674,508 to DeCote; U.S. Pat. No. 5,213,098 to Bennett et al.; U.S. Patent Application 2003/0074029 of Deno et al.; U.S. Patent Application 2004/0049118 of Ideker at al.; and U.S. Patent Application 2004/0049235 of Deno et al.

Figure 4:
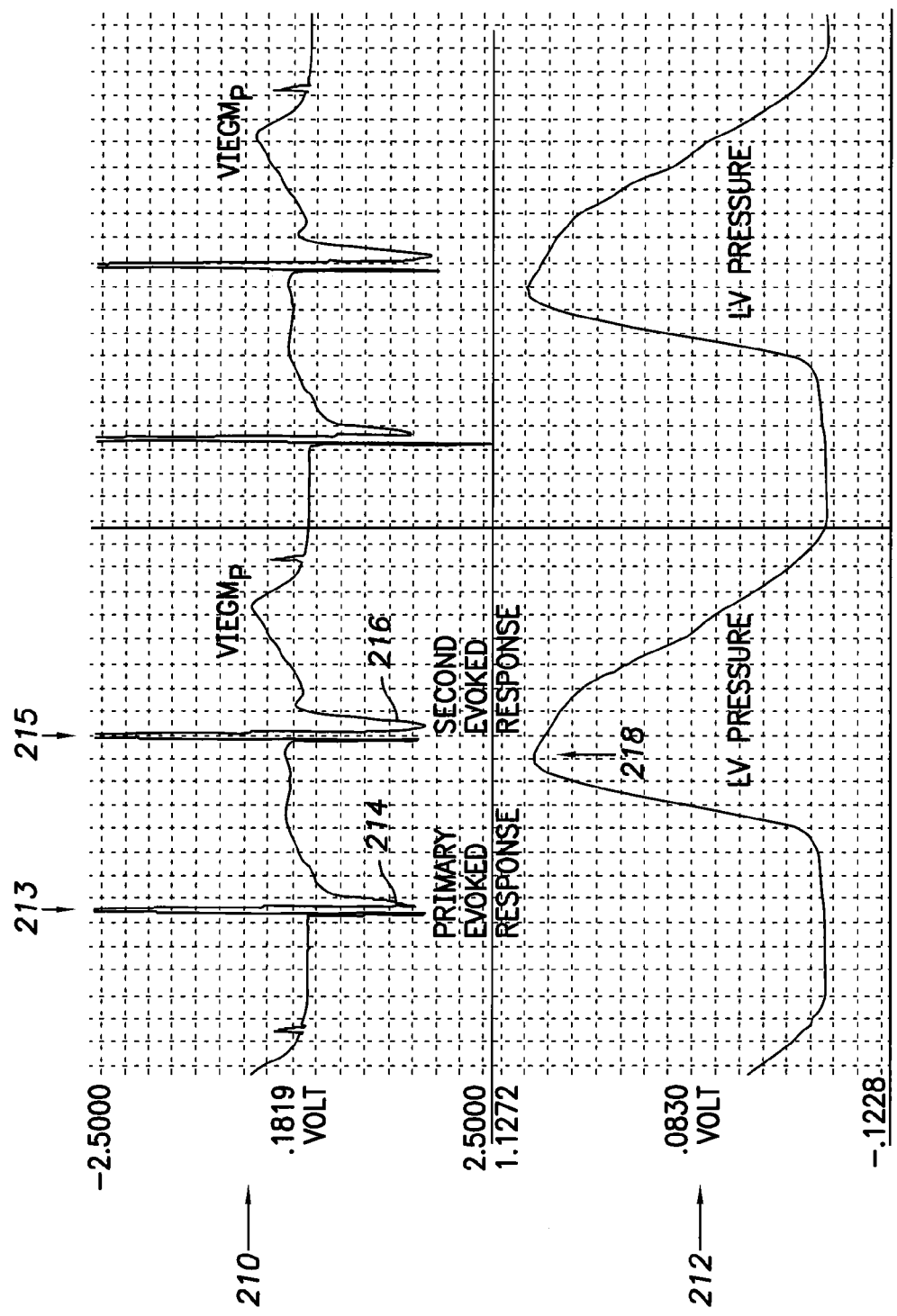
FIG. 4 is a diagram of exemplary ventricular IEGM traces and LV pressure traces, particularly illustrating the use of optimal inter-pulse intervals during paired pacing, in accordance with the general techniques of FIG. 3.
Figure 5:
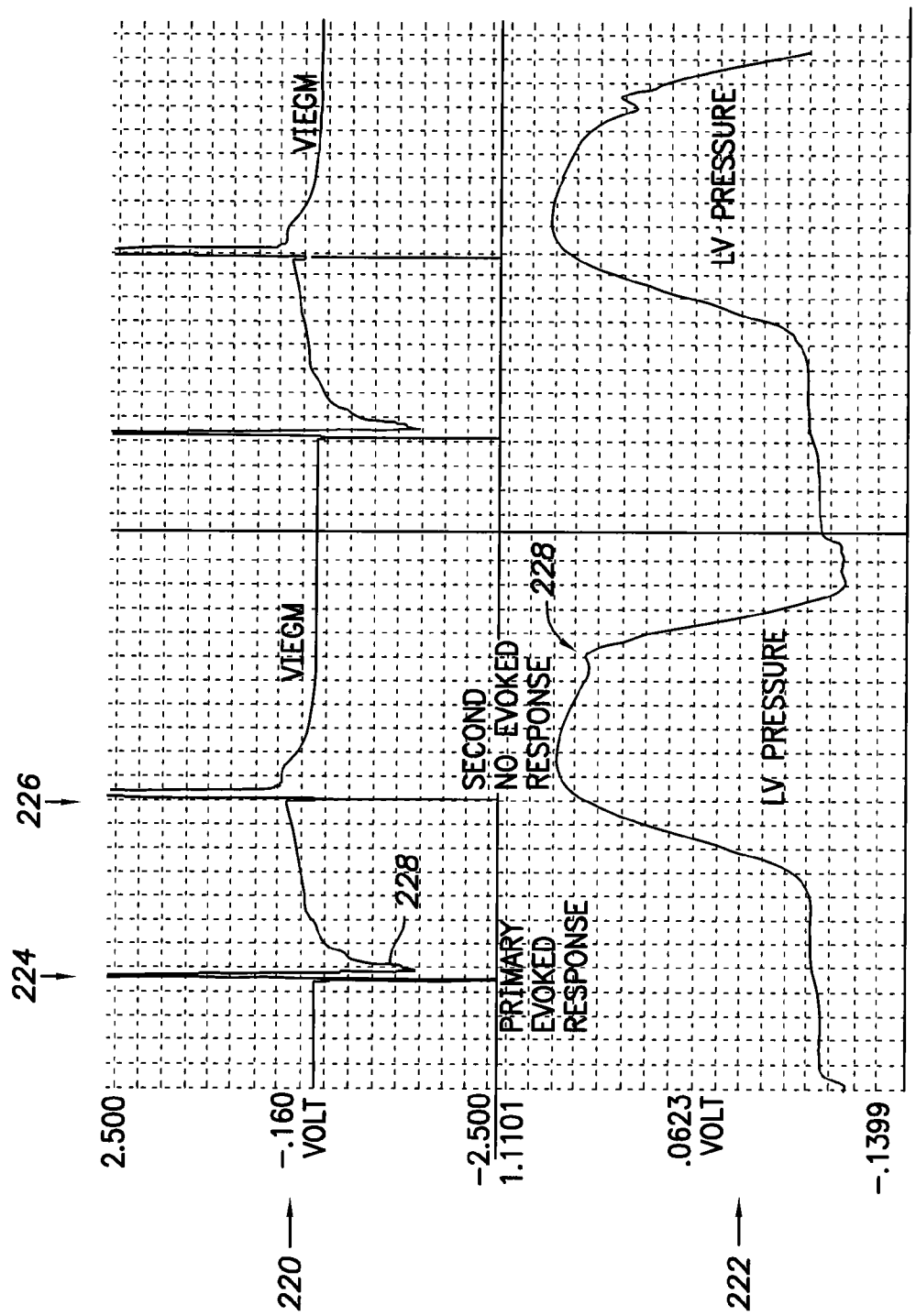
FIG. 5 is a diagram of exemplary ventricular IEGM traces and LV pressure traces, particularly illustrating circumstances wherein a second pulse of a pair of pulses fails to capture.
Figure 6:
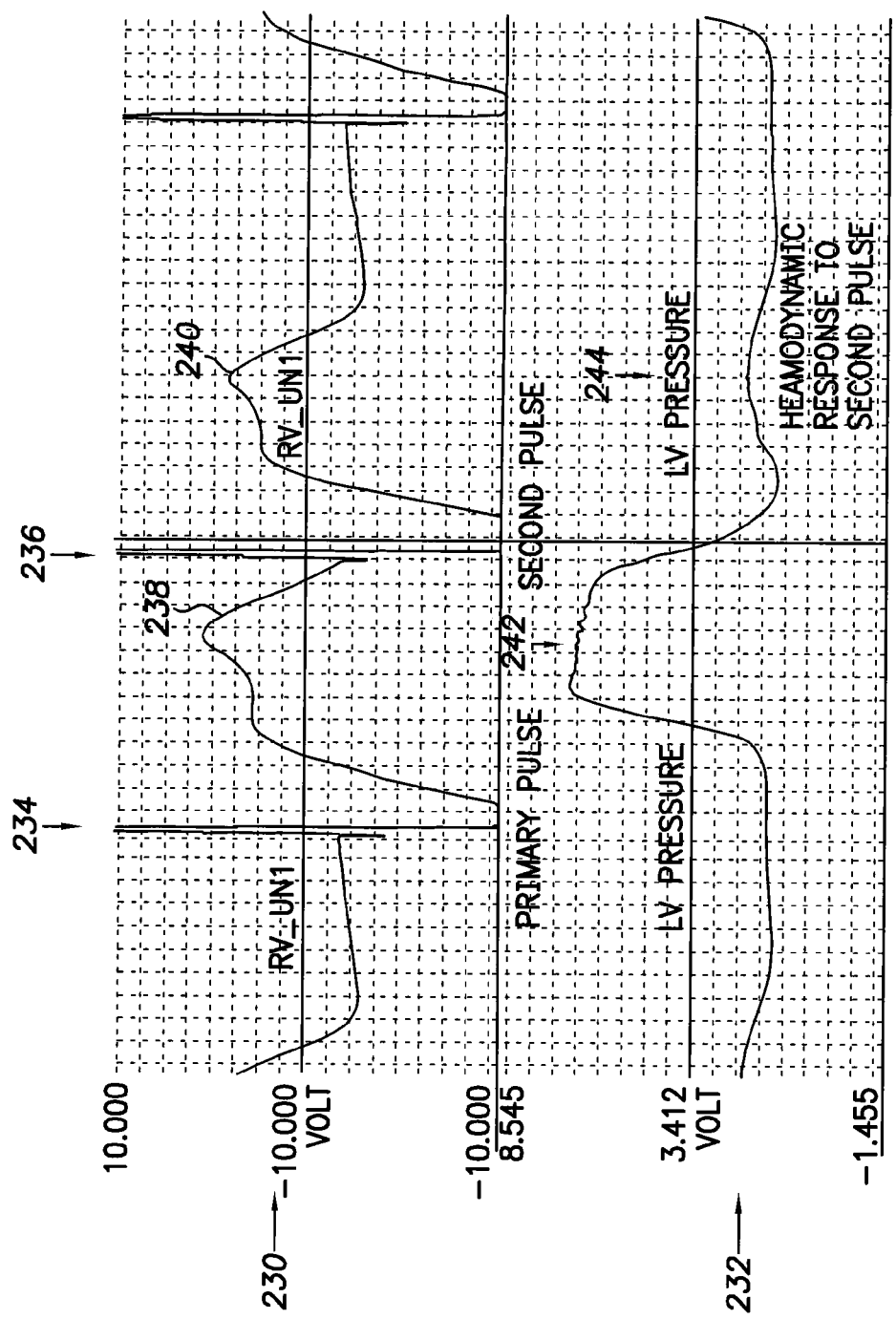
FIG. 6 is a diagram of exemplary ventricular IEGM traces and LV pressure traces, particularly illustrating the use of a non-optimal inter-pulse interval during paired pacing, resulting in a separate hemodynamic response triggered by the secondary pulse.

The effects of the optimization technique of FIG. 3 are illustrated within FIGS. 4-6. Referring first to FIG. 4, a ventricular IEGM trace 210 is shown alongside a trace of LV pressure 212 for an example involving paired pacing. In this example, the inter-pulse interval is optimized in accordance with techniques of FIG. 3 to ensure that the evoked response associated with the second pulse of the pair is wider than that of the primary pulse. The evoked response of a primary pulse 213 is identified by reference 214; the evoked response of a secondary pulse 215 is denoted by reference from 216. The LV pressure profile resulting from the paired pulses exhibits only a single high peak 218, indicative of effective ventricular pumping. This is in contrast with traces of FIG. 5, which illustrates a circumstance in which the second pulse of the pair of pulses fails to capture because it is delivered too soon, i.e. the inter-pulse interval is too short. More specifically, FIG. 5 illustrates a ventricular IEGM trace 220 along with a corresponding LV pressure trace 222 for a pair of pulses 224 and 226 delivered subject to an inter-pulse interval, which is too short. The first pulse evokes a response, denoted by reference 228. The second pulse, however, fails to evoke a response. Hence, the (nonexistent) evoked response of second pulse is not wider than the evoked response of the first pulse, causing degradation in the left ventricular pressure profile. As can be seen, the LV pressure profile has a peak magnitude less than that of FIG. 4 and includes a notch followed by a secondary peak 228, indicative of non-optimal ventricular pumping, possibly due to asynchronous contractions of the left and right ventricles or other ventricular dyssynchronies.

FIG. 6 illustrates an example wherein the second pulse is properly captured but the inter-pulse interval is too long. Again, a pair of traces is illustrated—including a ventricular IEGM trace 230 and a LV pressure trace 232. A pair of ventricular pulses 234 and 236 is delivered subject to an inter-pulse interval, which is too long. Primary pulse 234 triggers an evoked response 238; whereas secondary pulse 236 triggers a second evoked response 240. The resulting profile in LV pressure exhibits a first peak 242 followed by a shallower, secondary peak 244 representative of the hemodynamic response of the ventricles to the second pulse. As a result of the failure of the ventricles to contract optimally, the peak ventricular pressure is lower than that of FIG. 4. Also, the area (or integral) of the overall ventricular pressure curve is smaller, typically indicating less blood pumped during the beat.

Although FIG. 4 is illustrative of the benefits of paired pacing pulses, similar benefits may be found when applying the width-based technique to coupled ventricular pacing pulses as well. Also, although the traces illustrated in FIGS.

4-6 are derived from test subjects under clinical conditions, similar benefits are expected to be achieved within actual patients under real-world conditions.

Thus, FIGS. 3-6 illustrate techniques for use with paired/coupled pacing pulses for achieving improvements in LV pressure by optimizing the paired/coupled pacing interval. As noted, the techniques of FIGS. 3-6 do not require the use of dynamic overdrive/underdrive pacing techniques, as exploited in the techniques of FIGS. 1-2. Nevertheless, the combination of both techniques, i.e. the use of dynamic overdrive/underdrive pacing while employing an optimal inter-pulse interval, can achieve still greater benefits. This is illustrated within FIG. 7.

Figure 7:
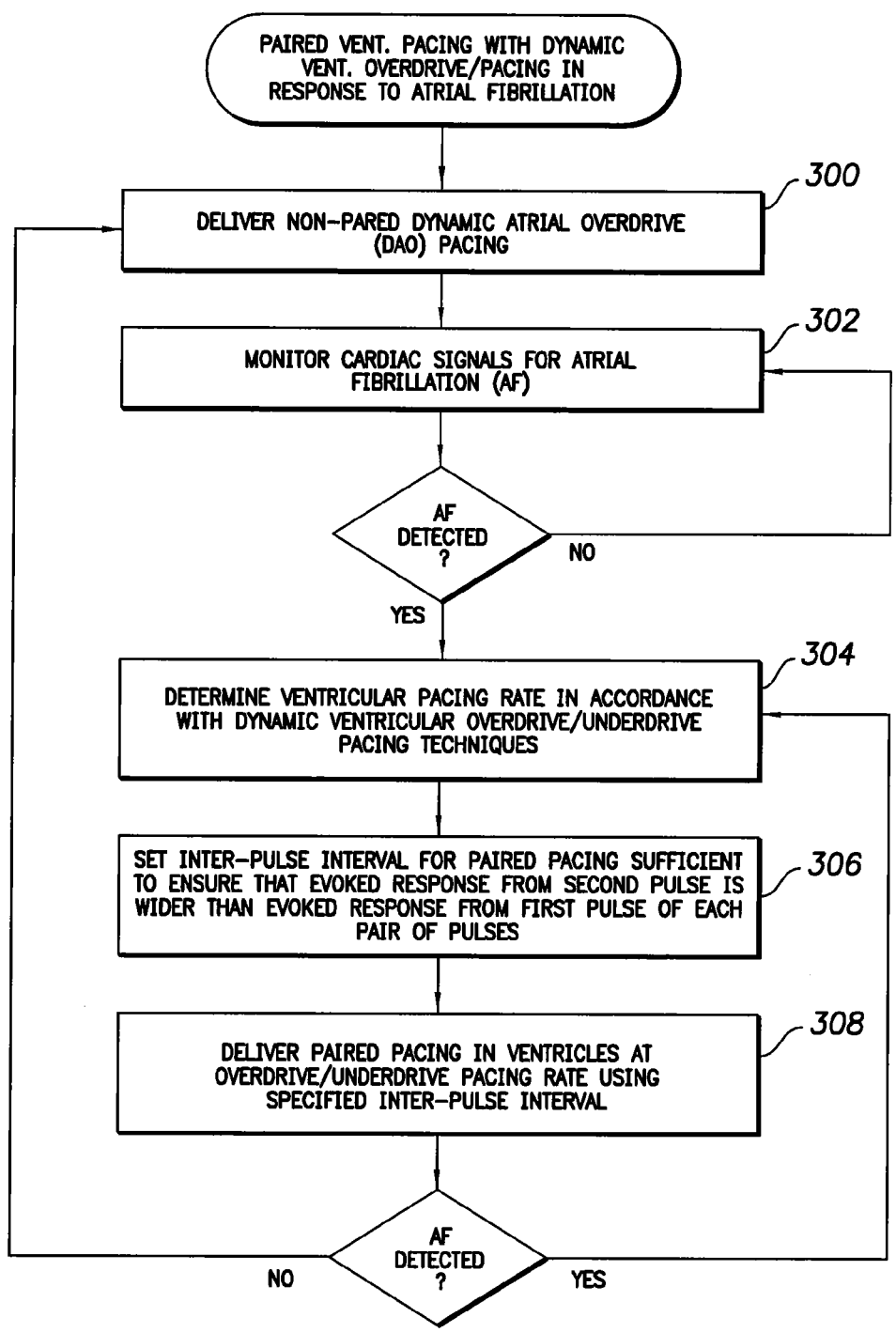
FIG. 7 is a flow diagram providing an exemplary technique for performing paired/coupled pacing along with dynamic ventricular overdrive/underdrive pacing during AF while using an optimal inter-pulse interval, in accordance with the techniques of both FIGS. 1 and 3.

Dynamic Ventricular Overdrive/Underdrive Pacing with Paired Pacing While Using Optimal Inter-Pulse Intervals Turning now to FIG. 7, an exemplary technique is illustrated wherein dynamic ventricular overdrive/underdrive pacing is performed during AF using paired pulses and wherein an optimal inter-pulse interval is also exploited. Beginning at step 300, the implantable device delivers non-paired DAO pacing in the atria in an attempt suppress AF. The device monitors cardiac signals, at step 302, to detect any episodes of AF that occur despite DAO. Assuming AF is detected then, at step 304, the device determines the rate for ventricular pacing in accordance with dynamic ventricular overdrive/underdrive pacing techniques, such as those described above with reference to FIGS. 1-2. At step 306, the device sets the interval for paired pacing to a value sufficient to ensure that the evoked response from the secondary pulse is wider than the evoked response from the primary pulse, in accordance with the techniques of FIGS. 3-6. At step 308, the device then begins delivering paired pacing pulses to the ventricles at the overdrive rate determined at step 304 and subject to the inter-pulse interval specified at step 306. Preferably, the optimal interval for a given overdrive rate is determined in advance for the particular patient so that, at step 306, the device need only look-up the appropriate inter-pulse interval. A lookup table may be provided with an optimal inter-pulse interval for each of a set of ranges of ventricular overdrive rates. Alternatively, as noted above, a single optimal inter-pulse interval may be stored for use at a base pacing rate. The device then calculates the appropriate rate for the current overdrive rate determined step 304 by applying a predetermined factoring coefficient. In any case, so long as AF continues, steps 304-308 are repeated to periodically update the overdrive rate in accordance with dynamic ventricular overdrive/underdrive pacing techniques while adjusting the inter-pulse interval of the paired pulses to maintain the optimal interval for the given overdrive rate. Once AF terminates, processing returns to step 300 wherein otherwise normal non-paired DAO pacing resumes. (Note that dynamic ventricular overdrive/underdrive pacing is not performed during AF for the purpose of terminating AF, but primarily for the purpose of mitigating its effects and for preventing ventricular arrhythmias from being triggered.)

In other implementations, non-overdrive/non-paired paired pacing is performed at step 300. In still other implementations, DAO pacing with paired atrial pulses is instead performed at step 300. As can be appreciated, there are a wide range of implementations that exploit various combinations of dynamic overdrive/underdrive pacing, paired pacing, coupled pacing, and the like, either with or without inter-pulse optimization.

Exemplary Pacer/ICD

Figure 8:
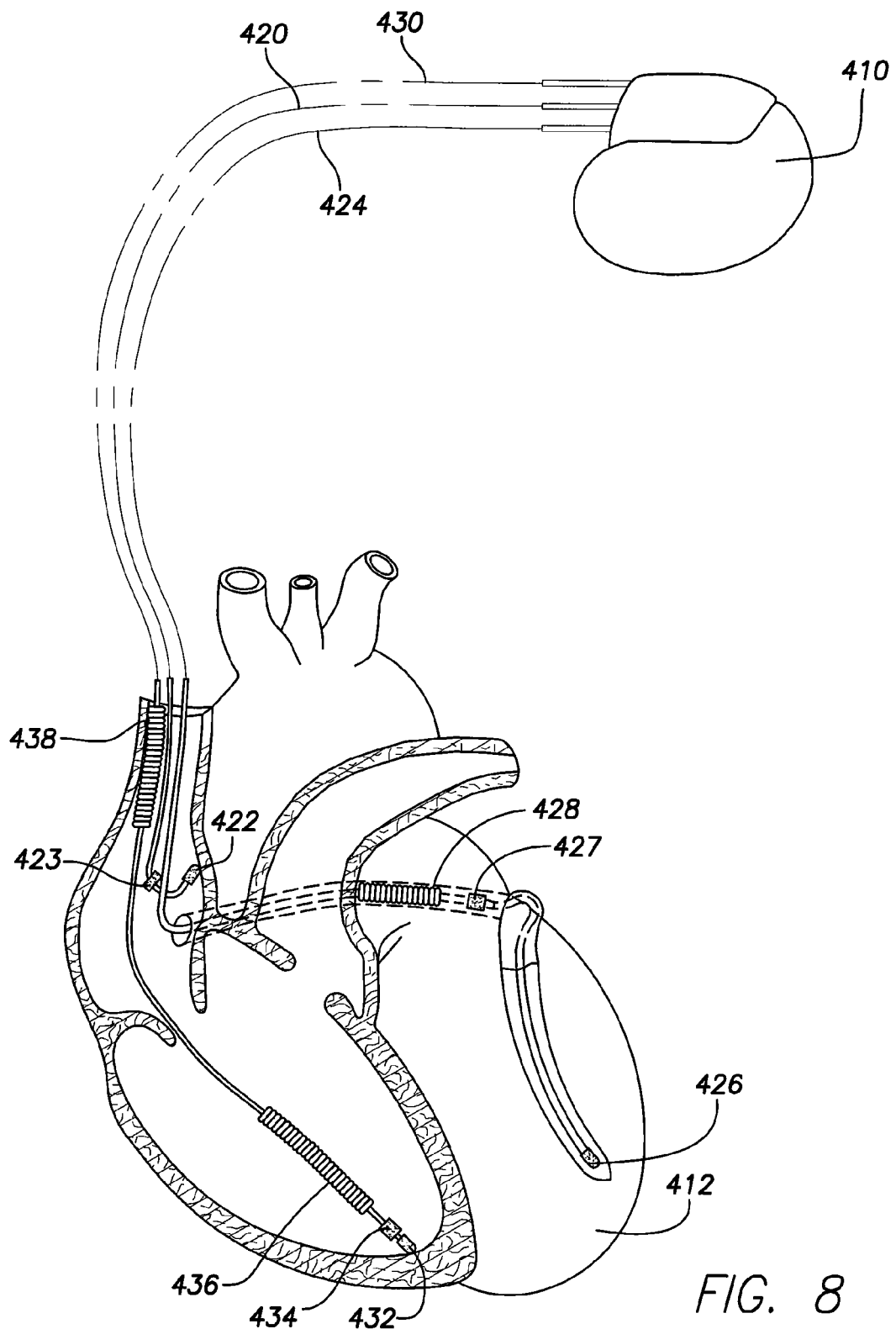
FIG. 8 is a simplified diagram illustrating an implantable stimulation device, equipped to perform the techniques of FIGS. 1-7, with leads implanted into the heart of a patient.

For the sake of completeness, a description of an exemplary pacer/ICD will now be provided, which is capable of implementing the aforementioned pacing techniques. FIG. 8 provides a simplified block diagram of a pacer/ICD 410, which is a dual-chamber stimulation device capable of treating both fast and slow arrhythmias with stimulation therapy, including cardioversion, defibrillation, and pacing stimulation. To provide atrial chamber pacing stimulation and sensing, pacer/ICD 410 is shown in electrical communication with a heart 412 by way of a left atrial lead 420 having an atrial tip electrode 422 and an atrial ring electrode 423 implanted in the atrial appendage. Pacer/ICD 410 is also in electrical communication with the heart by way of a right ventricular lead 430 having, in this embodiment, a ventricular tip electrode 432, a right ventricular ring electrode 434, a right ventricular (RV) coil electrode 436, and a superior vena cava (SVC) coil electrode 438. Typically, the right ventricular lead 430 is transvenously inserted into the heart so as to place the RV coil electrode 436 in the right ventricular apex, and the SVC coil electrode 438 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 410 is coupled to a "coronary sinus" lead 424 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 424 is designed to receive atrial and ventricular cardiac signals and to deliver left ventricular pacing therapy using at least a left ventricular tip electrode 426, left atrial pacing therapy using at least a left atrial ring electrode 427, and shocking therapy using at least a left atrial coil electrode 428. With this configuration, biventricular pacing can be performed. Although only three leads are shown in FIG. 8, it should also be understood that additional stimulation leads (with one or more pacing, sensing and/or shocking electrodes) may be used in order to efficiently and effectively provide pacing stimulation to the left side of the heart or atrial cardioversion and/or defibrillation.

Figure 9:
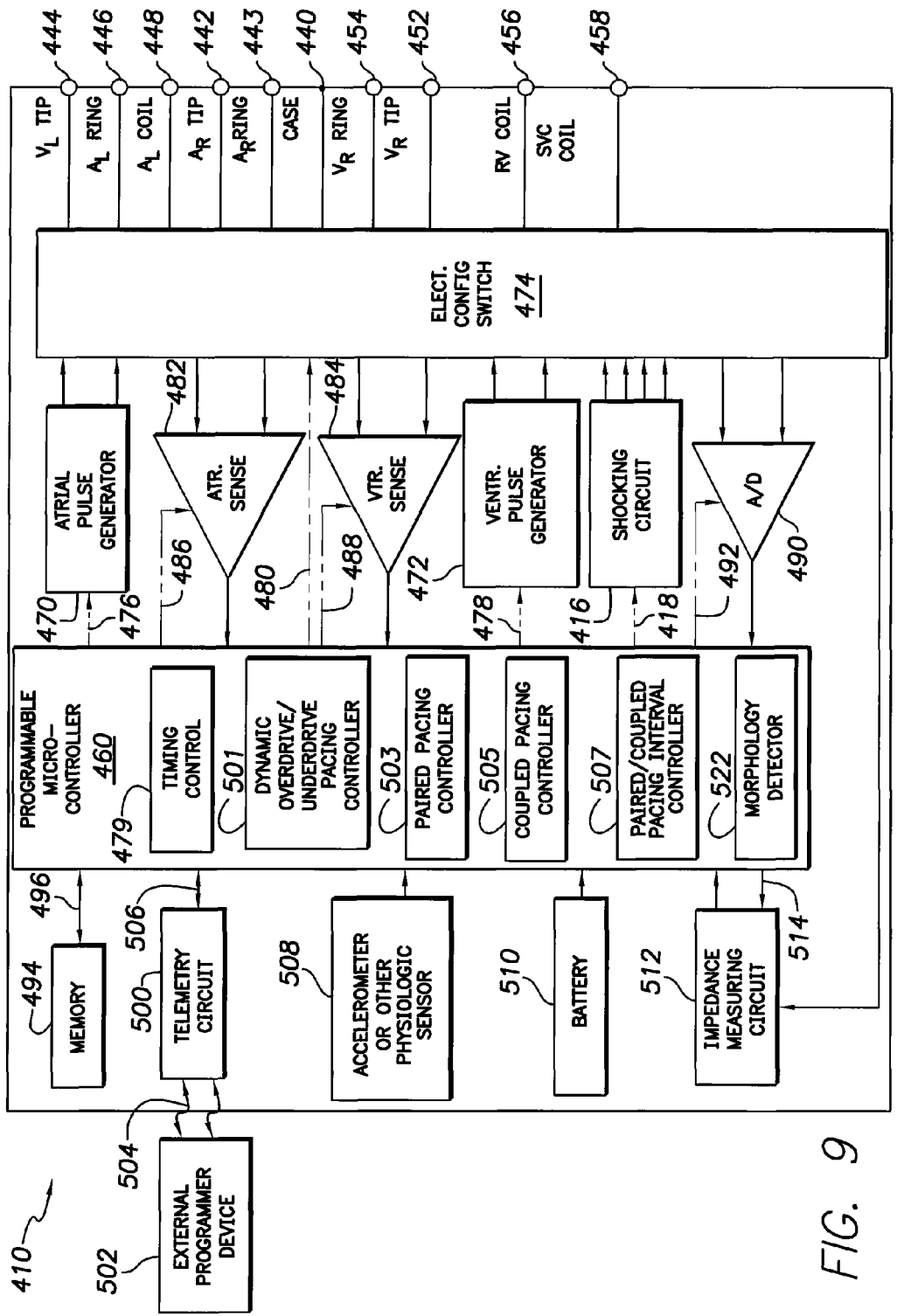
FIG. 9 is a functional block diagram of the device of FIG. 8 illustrating basic elements of the device and particularly illustrating components for controlling paired pacing, coupled pacing, and dynamic ventricular overdrive/underdrive pacing in accordance with the techniques of FIGS. 1-7.

A simplified block diagram of internal components of pacer/ICD 410 is shown in FIG. 9. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation as well as providing for the aforementioned apnea detection and therapy.

The housing 440 for pacer/ICD 410, shown schematically in FIG. 9, is often referred to as the "can", "case" or "case electrode" and may be programmably selected to act as the return electrode for all "unipolar" modes. The housing 440 may further be used as a return electrode alone or in combination with one or more of the coil electrodes, 428, 436 and 438, for shocking purposes. The housing 440 further includes a connector (not shown) having a plurality of terminals, 442, 443, 444, 446, 448, 452, 454, 456 and 458 (shown schematically and, for convenience, the names of the electrodes to which they are connected are shown next to the terminals). As such, to achieve right atrial sensing and pacing, the connector includes at least a right atrial tip terminal ($A_R$ TIP) 442 adapted for connection to the atrial tip electrode 422 and a right atrial ring ($A_R$ RING) electrode 443 adapted for connection to right atrial ring electrode 423. To achieve left chamber sensing, pacing and shocking, the connector includes at least a left ventricular tip terminal ($V_L$ TIP) 444, a left atrial ring terminal ($A_L$ RING) 446, and a left atrial shocking terminal ($A_L$ COIL) 448, which are adapted for connection to the left ventricular ring electrode 426, the left atrial ring electrode 427, and the left atrial coil electrode 428, respectively. To support right chamber sensing, pacing and shocking, the connector further includes a right ventricular tip terminal ($V_R$ TIP) 452, a right ventricular ring terminal ($V_R$ RING) 454, a right ventricular shocking terminal ($R_V$ COIL) 456, and an SVC shocking terminal (SVC COIL) 458, which are adapted for connection to the right ventricular tip electrode 432, right ventricular ring electrode 434, the RV coil electrode 436, and the SVC coil electrode 438, respectively.

At the core of pacer/ICD 410 is a programmable microcontroller 460, which controls the various modes of stimulation therapy. As is well known in the art, the microcontroller 460 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 460 includes the ability to process or monitor input signals (data) as controlled by a program code stored in a designated block of memory. The details of the design and operation of the microcontroller 460 are not critical to the invention. Rather, any suitable microcontroller 460 may be used that carries out the functions described herein. The use of microprocessor-based control circuits for performing timing and data analysis functions are well known in the art.

As shown in FIG. 9, an atrial pulse generator 470 and a ventricular pulse generator 472 generate pacing stimulation pulses for delivery by the right atrial lead 420, the right ventricular lead 430, and/or the coronary sinus lead 424 via an electrode configuration switch 474. It is understood that in order to provide stimulation therapy in each of the four chambers of the heart, the atrial and ventricular pulse generators, 470 and 472, may include dedicated, independent pulse generators, multiplexed pulse generators or shared pulse generators. The pulse generators, 470 and 472, are controlled by the microcontroller 460 via appropriate control signals, 476 and 478, respectively, to trigger or inhibit the stimulation pulses.

The microcontroller 460 further includes timing control circuitry 479 used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 474 includes a plurality of switches for connecting the desired electrodes to the appropriate I/O circuits, thereby providing complete electrode programmability. Accordingly, the switch 474, in response to a control signal 480 from the microcontroller 460, determines the polarity of the stimulation pulses (e.g., unipolar, bipolar, combipolar, etc.) by selectively closing the appropriate combination of switches (not shown) as is known in the art.

Atrial sensing circuits 482 and ventricular sensing circuits 484 may also be selectively coupled to the right atrial lead 420, coronary sinus lead 424, and the right ventricular lead 430, through the switch 474 for detecting the presence of cardiac activity in each of the four chambers of the heart. Accordingly, the atrial (ATR. SENSE) and ventricular (VTR. SENSE) sensing circuits, 482 and 484, may include dedicated sense amplifiers, multiplexed amplifiers or shared amplifiers. The switch 474 determines the "sensing polarity" of the cardiac signal by selectively closing the appropriate switches, as is also known in the art. In this way, the clinician may program the sensing polarity independent of the stimulation polarity. Each sensing circuit, 482 and 484, preferably employs one or more low power, precision amplifiers with programmable gain and/or automatic gain control, bandpass filtering, and a threshold detection circuit, as known in the art, to selectively sense the cardiac signal of interest. The automatic gain control enables pacer/ICD 410 to deal effectively with the difficult problem of sensing the low amplitude signal characteristics of atrial or ventricular fibrillation. The outputs of the atrial and ventricular sensing circuits, 482 and 484, are connected to the microcontroller 460 which, in turn, are able to trigger or inhibit the atrial and ventricular pulse generators, 470 and 472, respectively, in a demand fashion in response to the absence or presence of cardiac activity in the appropriate chambers of the heart.

For arrhythmia detection, pacer/ICD 410 utilizes the atrial and ventricular sensing circuits, 482 and 484, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 460 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 490. The data acquisition system 490 is configured to acquire intracardiac electrogram signals, convert the raw analog data into a digital signal, and store the digital signals for later processing and/or telemetric transmission to an external device 502. The data acquisition system 490 is coupled to the right atrial lead 420, the coronary sinus lead 424, and the right ventricular lead 430 through the switch 474 to sample cardiac signals across any pair of desired electrodes. The microcontroller 460 is further coupled to a memory 494 by a suitable data/address bus 496, wherein the programmable operating parameters used by the microcontroller 460 are stored and modified, as required, in order to customize the operation of pacer/ICD 410 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 410 may be non-invasively programmed into the memory 494 through a telemetry circuit 500 in telemetric communication with the external device 502, such as a programmer, transtelephonic transceiver or a diagnostic system analyzer. The telemetry circuit 500 is activated by the microcontroller by a control signal 506. The telemetry circuit 500 advantageously allows intracardiac electrograms and status information relating to the operation of pacer/ICD 410 (as contained in the microcontroller 460 or memory 494) to be sent to the external device 502 through an established communication link 504. Pacer/ICD 410 further includes an accelerometer or other physiologic sensor 508, commonly referred to as a "rate-responsive" sensor because it is typically used to adjust pacing stimulation rate according to the exercise state of the patient. However, the physiological sensor 508 may further be used to detect changes in cardiac output, changes in the physiological condition of the heart, or diurnal changes in activity (e.g., detecting sleep and wake states) and to detect arousal from sleep. Accordingly, the microcontroller 460 responds by adjusting the various pacing parameters (such as rate, AV/PV delay, V-V Delay, etc.) at which the atrial and ventricular pulse generators, 470 and 472, generate stimulation pulses. While shown as being included within pacer/ICD 410, it is to be understood that the physiologic sensor 508 may also be external to pacer/ICD 410, yet still be implanted within or carried by the patient. A common type of rate responsive sensor is an activity sensor incorporating an accelerometer or a piezoelectric crystal, which is mounted within the housing 440 of pacer/ICD 410. Other types of physiologic sensors are also known, for example, sensors that sense the oxygen content of blood, respiration rate and/or minute ventilation, pH of blood, ventricular gradient, etc.

Insofar as dynamic overdrive/underdrive pacing and paired/coupled pacing is concerned, the microcontroller includes a dynamic overdrive/underdrive pacing controller 501, a paired pacing controller 503, a coupled pacing controller 505 and a paired/coupled pacing interval controller 507. These units operate in accordance with the techniques described above with reference to FIGS. 1-7. Although shown as being part of the microcontroller, these units may instead be implemented as components separate from the microcontroller.

The pacer/ICD additionally includes a battery 510, which provides operating power to all of the circuits shown in FIG. 9. The battery 510 may vary depending on the capabilities of pacer/ICD 410. If the system only provides low voltage therapy, a lithium iodine or lithium copper fluoride cell may be utilized. For pacer/ICD 410, which employs shocking therapy, the battery 510 must be capable of operating at low current drains for long periods, and then be capable of providing high-current pulses (for capacitor charging) when the patient requires a shock pulse. The battery 510 must also have a predictable discharge characteristic so that elective replacement time can be detected. Accordingly, pacer/ICD 410 is preferably capable of high voltage therapy and appropriate batteries.

As further shown in FIG. 9, pacer/ICD 410 is shown as having an impedance measuring circuit 512 which is enabled by the microcontroller 460 via a control signal 514. Herein, thoracic impedance is primarily detected for use in tracking thoracic respiratory oscillations. Other uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, etc. The impedance measuring circuit 120 is advantageously coupled to the switch 74 so that any desired electrode may be used.

In the case where pacer/ICD 410 is intended to operate as an implantable cardioverter/defibrillator (ICD) device, it detects the occurrence of an arrhythmia, and, if so programmed, automatically applies an appropriate electrical shock therapy to the heart aimed at terminating the detected arrhythmia. To this end, the microcontroller 460 further controls a shocking circuit 516 by way of a control signal 518. The shocking circuit 516 generates shocking pulses of low (up to 0.5 joules), moderate (0.5-10 joules) or high energy (11 to 40 joules), as controlled by the microcontroller 460. Such shocking pulses are applied to the heart of the patient through at least two shocking electrodes, and as shown in this embodiment, selected from the left atrial coil electrode 428, the RV coil electrode 436, and/or the SVC coil electrode 438. The housing 440 may act as an active electrode in combination with the RV electrode 436, or as part of a split electrical vector using the SVC coil electrode 438 or the left atrial coil electrode 428 (i.e., using the RV electrode as a common electrode). Preferably, during AF, dynamic ventricular overdrive/underdrive pacing with paired pacing pulses is performed, as discussed above. Should a cardioversion shock be desired, perhaps because AF does not terminate within an acceptable period of time, the device deactivates dynamic ventricular overdrive/underdrive pacing and instead delivers the cardioversion shock. Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 460 is capable of controlling the synchronous or asynchronous delivery of the shocking pulses.

In addition, the stimulation device may be configured to perform Automatic Mode Switching (AMS) wherein the pacemaker reverts from a tracking mode such as a VDD or DDD mode to a nontracking mode such as VVI or DDI mode. VDD, DDD, VVI and DDI are standard device codes that identify the mode of operation of the device. DDD indicates a device that senses and paces in both the atria and the ventricles and is capable of both triggering and inhibiting functions based upon events sensed in the atria and the ventricles. VDD indicates a device that sensed in both the atria and ventricles but only paces in the ventricles. A sensed event on the atrial channel triggers ventricular outputs after a programmable delay, the pacemaker's equivalent of a PR interval. WI indicates that the device is capable of pacing and sensing only in the ventricles and is only capable of inhibiting the functions based upon events sensed in the ventricles. DDI is identical to DDD except that the device is only capable of inhibiting functions based upon sensed events, rather than triggering functions. As such, the DDI mode is a non-tracking mode precluding its triggering ventricular outputs in response to sensed atrial events. Numerous other device modes of operation are possible, each represented by standard abbreviations of this type.

What have been described are various techniques for paired/coupled pacing and dynamic overdrive/underdrive pacing. Although described primarily with reference to an example wherein the implanted device is an ICD, principles of the invention are applicable to other implanted cardiac stimulation devices as well such as pacemakers without defibrillation capability. The various functional components of the exemplary systems may be implemented using any appropriate technology including, for example, microprocessors running software programs or application specific integrated circuits (ASICs) executing hard-wired logic operations. The exemplary embodiments of the invention described herein are merely illustrative of the invention and should not be construed as limiting the scope of the invention.

What is claimed is:

1. In an implantable cardiac stimulation device for implant within a patient, a method comprising the steps of:
delivering paired pacing pulses to a chamber of the heart of the patient at an overdrive/underdrive pacing rate, wherein each of the paired pacing pulses comprises a primary pulse and a secondary pulse separated by an interval, and the interval between the primary pulse and the secondary pulse is such that there is no intrinsic depolarization of the chamber during the interval;
for one of the delivered paired pacing pulses, measuring the width of an evoked response of the chamber of the heart resulting from the primary pulse and measuring the width of an evoked response of the chamber of the heart resulting from the secondary pulse;
if the width of the evoked response resulting from the secondary pulse is less than the width of the evoked response resulting from the primary pulse, then adjusting the interval between the primary pulse and the secondary pulse of subsequent paired pacing pulses, and repeating the delivering, the measuring and the adjusting until the interval between the primary pulse and the secondary pulse of subsequent paired pacing pulses is at a duration sufficient to ensure that the width of the evoked response resulting from the secondary pulse is greater than the width of the evoked response resulting from the primary pulse.

2. The method of claim 1 wherein the chamber of the heart is a ventricle.

3. The method of claim 1 wherein delivering paired pacing pulses is performed only up to a predetermined maximum overdrive rate.

4. The method of claim 1 wherein delivering paired pacing pulses is performed only down to a predetermined minimum underdrive rate.

5. The method of claim 1 wherein delivering paired pacing pulses comprises:
pacing the heart at an overdrive/underdrive pacing rate selected to permit the detection of at least some intrinsic ventricular pulses; and
dynamically adjusting the overdrive/underdrive pacing rate based on the intrinsic ventricular pulses.

6. The method of claim 1 further including an initial step of detecting an episode of atrial fibrillation (AF) and wherein delivering paired pacing pulses is only applied to the ventricles and only performed during an episode of AF.

7. The method of claim 6 further including delivering dynamic overdrive/underdrive pacing to the atria using non-paired pacing pulses during periods of time when AF is not detected.

8. The method of claim 6 wherein the device is capable of performing a mode switch from a tracking mode to a non-tracking mode and is also capable of dynamic overdrive/underdrive pacing in the atria with non-paired pulses and wherein the method comprises the additional step, performed in accordance with a mode switch, of switching from dynamic overdrive/underdrive pacing in the atria with non-paired pulses to dynamic overdrive/underdrive pacing in the ventricles with paired pacing pulses.

9. The method of claim 1 wherein delivering paired pacing pulses is performed so as to achieve a rate below an intrinsic rate.

10. The method of claim 1 wherein measuring the width of an evoked response of the chamber of the heart resulting from the primary pulse and measuring the width of an evoked response of the chamber of the heart resulting from the secondary pulse comprises:
calculating first and second paced depolarization integrals (PDIs) associated, respectively, with the evoked responses of the primary and secondary pacing pulses; and
determining the widths of the evoked responses of the primary and secondary pacing pulses based on the first and second PDIs.

11. The method of claim 1 wherein adjusting the interval between primary and secondary pacing pulses comprises:
setting the interval to the shortest duration that ensures that the secondary pulse does not trigger a mechanical contraction of a chamber of the heart to which it is applied.

12. The method of claim 1 wherein the overdrive/underdrive pacing rate is specified by an interval between consecutive primary pulses.

13. The method of claim 1 further comprising the initial steps of:
detecting for an episode of atrial fibrillation; and
in the absence of atrial fibrillation, delivering overdrive pacing in an atria.

14. The method of claim 13, wherein the overdrive pacing is paired pacing overdrive pacing.

15. The method of claim 13, wherein the overdrive pacing is non-paired overdrive pacing.

16. The method of claim 13, wherein upon detection of atrial fibrillation, the chamber of a heart is a ventricle.

17. In an implantable cardiac stimulation device for implant within a patient, a system comprising:
a paired pacing controller operative to deliver paired pacing pulses at an overdrive/underdrive pacing rate to a chamber of the heart of the patient, wherein each of the paired pacing pulses comprises a primary pulse and a secondary pulse separated by an interval, and the interval between the primary pulse and the secondary pulse is such that there is no intrinsic depolarization of the chamber during the interval; and
a paired pacing interval controller operative to, for one of the delivered paired pacing pulses, measure the width of an evoked response of the chamber of the heart resulting from the primary pulse and measure the width of an evoked response of the chamber of the heart resulting from the secondary pulse; the interval controller further operative to, if the width of the evoked response resulting from the secondary pulse is less than the width of the evoked response resulting from the primary pulse, then adjust the interval between the primary pulse and the secondary pulse of subsequent paired pacing pulses, and repeatedly deliver, measure and adjust until the interval between the primary pulse and the secondary pulse of subsequent paired pacing pulses is sufficient to ensure that the width of the evoked response resulting from the secondary pulse is greater than the width of the evoked response resulting from the primary pulse;
wherein the paired pacing controller is further operative to deliver subsequent paired pacing pulses to the heart of the patient using the specified interval.

18. The device of claim 17 wherein to measure the width of an evoked response of the chamber of the heart resulting from the primary pulse and measure the width of an evoked response of the chamber of the heart resulting from the secondary pulse, the interval controller is operative to:

calculate first and second paced depolarization integrals (PDIs) associated, respectively, with the evoked responses of the primary and secondary pacing pulses; and determine the widths of the evoked responses of the primary and secondary pacing pulses based on the first and second PDIs.

19. The device of claim 17 wherein to adjust the interval between primary and secondary pacing pulses, the interval controller is operative to set the interval to the shortest duration that ensures that the secondary pulse does not trigger a mechanical contraction of a chamber of the heart to which it is applied.

* * * * *